United States Patent [19]
Beach et al.

[11] Patent Number: 5,244,389
[45] Date of Patent: Sep. 14, 1993

[54] DENTAL HANDPIECE HOLDER

[75] Inventors: Daryl R. Beach, Shizuoka; Katsumi Suzuki, Kyoto, both of Japan

[73] Assignee: Kabushiki Kaisha Morita Seisakusho, Kyoto, Japan

[21] Appl. No.: 841,824

[22] Filed: Feb. 26, 1992

[30] Foreign Application Priority Data

Mar. 15, 1991 [JP] Japan .................. 3-076980

[51] Int. Cl.$^5$ .................. A61C 1/02; A61C 1/08; A61G 15/00
[52] U.S. Cl. .................. 433/108; 433/79
[58] Field of Search .................. 433/49, 77, 79, 108, 433/109

[56] References Cited

U.S. PATENT DOCUMENTS

| | | | |
|---|---|---|---|
| D. 204,983 | 6/1966 | Stram et al. | D24/1 |
| 4,330,281 | 5/1982 | Hayashi | 433/108 |
| 4,952,146 | 8/1990 | Doty | 433/77 |
| 5,127,830 | 7/1992 | Sheridan et al. | 433/77 |
| 5,145,366 | 9/1992 | Janhunen | 433/77 |

FOREIGN PATENT DOCUMENTS

| | | | |
|---|---|---|---|
| 757953 | 12/1951 | Fed. Rep. of Germany | 433/77 |
| 2417955 | 10/1974 | Fed. Rep. of Germany | 433/77 |

OTHER PUBLICATIONS

Centura Handpiece System, S. S. White Company, Philadelphia, Pa., 1967.

*Primary Examiner*—John J. Wilson
*Assistant Examiner*—Cindy A. Cherichetti
*Attorney, Agent, or Firm*—Koda and Androlia

[57] ABSTRACT

A dental handpiece holder adapted such that the length of the handpiece holder for holding and accommodating a dental handpiece is shortened in the axial direction, whereby the main unit of the handpiece can be attached to and detached from the joint section of the handpiece for the purpose of replacement with one hand of an operator. Also a dental treatment assembly by use of the holder.

The handpiece holder comprising a gutter-shaped receiving seat, first and second grip sections extending from both side fringes of the receiving seat, contact sections formed at the leading ends of the first and second grip sections respectively and an engagement groove or projection extending across the contact sections or the peripheral areas thereof in the internal circumferential direction of the grip sections.

3 Claims, 7 Drawing Sheets

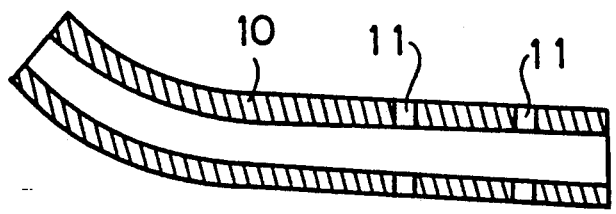
FIG.2
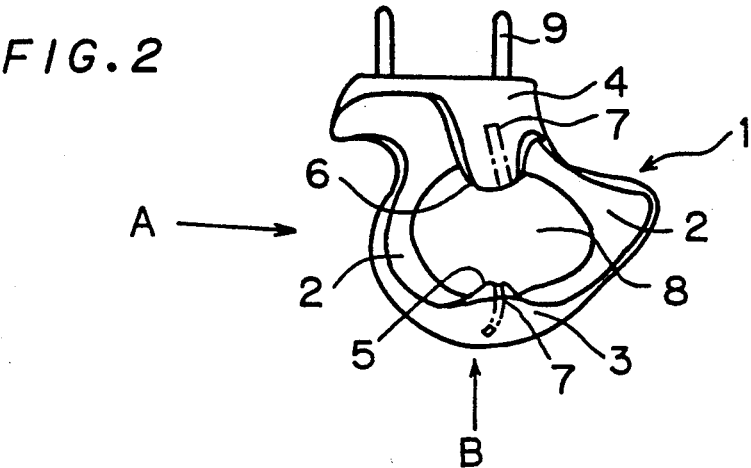
FIG.3
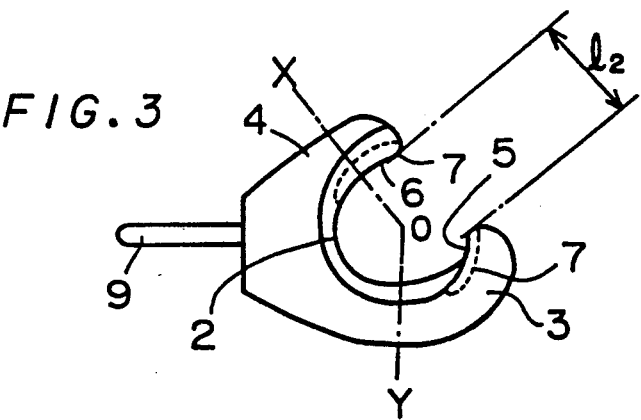
FIG.4
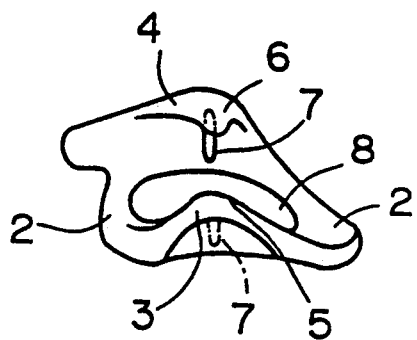

DENTAL HANDPIECE HOLDER

BACKGROUND OF THE INVENTION

1. Field of the invention

The present invention relates to a dental handpiece holder and a dental treatment assembly by use thereof.

2. Prior art

The applicant of the present invention has proposed a handpiece holder which can accommodate a handpiece in such a manner that the handpiece can be detached easily from the holder by operator's one hand holding the handpiece like a pencil during dental treatment but has no possibility of dropping from the holder and that the holder is scarcely subjected to accumulation of dust and dirt for enhanced sanitation as described in the Japanese Utility Model Application No. 55-51626 (Japanese Utility Model Publication No. 60-33939).

The holder is used to hold the handpiece in the horizontal or slightly inclined condition. It has a structure connecting the receiving section on its leading side and the receiving section on its trailing side, both receiving sections having a shape of a gutter. The receiving section on the leading side has three grip sections in total disposed on both sides of the receiving section on the leading side to hold the base section (rear side) of the grip section of the handpiece to be held like a pencil. In addition, the receiving section on the trailing side holds the large diameter handle section of the handpiece's rear section. This holder is thus relatively long in the axial direction and the handpiece is held in the relatively long range from the base section of the grip section to the large diameter handle section of the handpiece.

On the other hand, as disclosed in Japanese Patent Publication No. 53-1600, so-called multi-joint type handpieces have been developed, wherein each of the main units of various handpieces can be replaceably attached to the joint section connected to a tube containing pipes and wires used to supply pneumatic air, water, electricity and light for dental treatment or for driving such handpieces so that only the main unit of the handpiece can be replaced depending on the purpose of treatment. A system, wherein a handpiece's main unit with a built-in illumination unit can be replaced with a main unit without a built-in illumination unit very easily, has already been used practically for air turbine handpieces for example.

Although the dental handpiece described in the above-mentioned Japanese Utility Model Publication No. 60-33939 is superior as described above, it still has the following problems to be solved. As described above, the holder is relatively long in the axial direction and holds the handpiece in the long range from the grip section to the handle section of the handpiece. In addition, when the handpiece is attached to or detached from the holder, the handpiece slides in the axial direction along the receiving section of the holder. At the time of attaching or detaching the handpiece to or from the holder, in particular when attaching the handpiece to the holder, the operator's hand holding the handpiece like a pencil is apt to contact the holder. As a result, the operator's hand contaminated inside the mouth of a patient may contaminate the holder or on the contrary the contaminated holder may contaminate the operator's hand. Furthermore, it is troublesome to sterilize the holder since the holder has receiving sections on its leading and trailing sides and is relatively long in the axial direction.

SUMMARY OF THE INVENTION

To solve the above-mentioned problems, the objects of the present invention are to provide a dental handpiece holder which is short in the axial direction and also to provide a dental treatment assembly by use of the holder, which can securely hold a dental handpiece by using the handpiece holder shortened in the axial direction.

In the case of the multi-joint type handpiece wherein only the main unit of the handpiece is replaced depending on the treatment purpose, it is desired that the main unit of the handpiece can be attached and detached very easily for replacement by using the operator's one hand which holds the handpiece like a pencil, while the handpiece is attached to and retained in the holder. The further object of the present invention is to provide a dental handpiece holder which can meet these needs and a handpiece which can be used in combination with the dental handpiece holder. Another object of the present invention is to simplify the attaching and detaching of the handpiece holder so that the holder can be sterilized easily.

BRIEF DESCRIPTION OF THE DRAWINGS

FIG. 2 is a plan view of the handpiece holder of the present invention shown in FIG. 1, FIG. 3 is a side view of the handpiece holder shown in FIG. 2 taken in direction A indicated in FIG. 2, FIG. 4 is a side view of the handpiece holder shown in FIG. 3 taken in direction B indicated in FIG. 2.

DETAILED DESCRIPTION OF THE INVENTION

Figure 1:
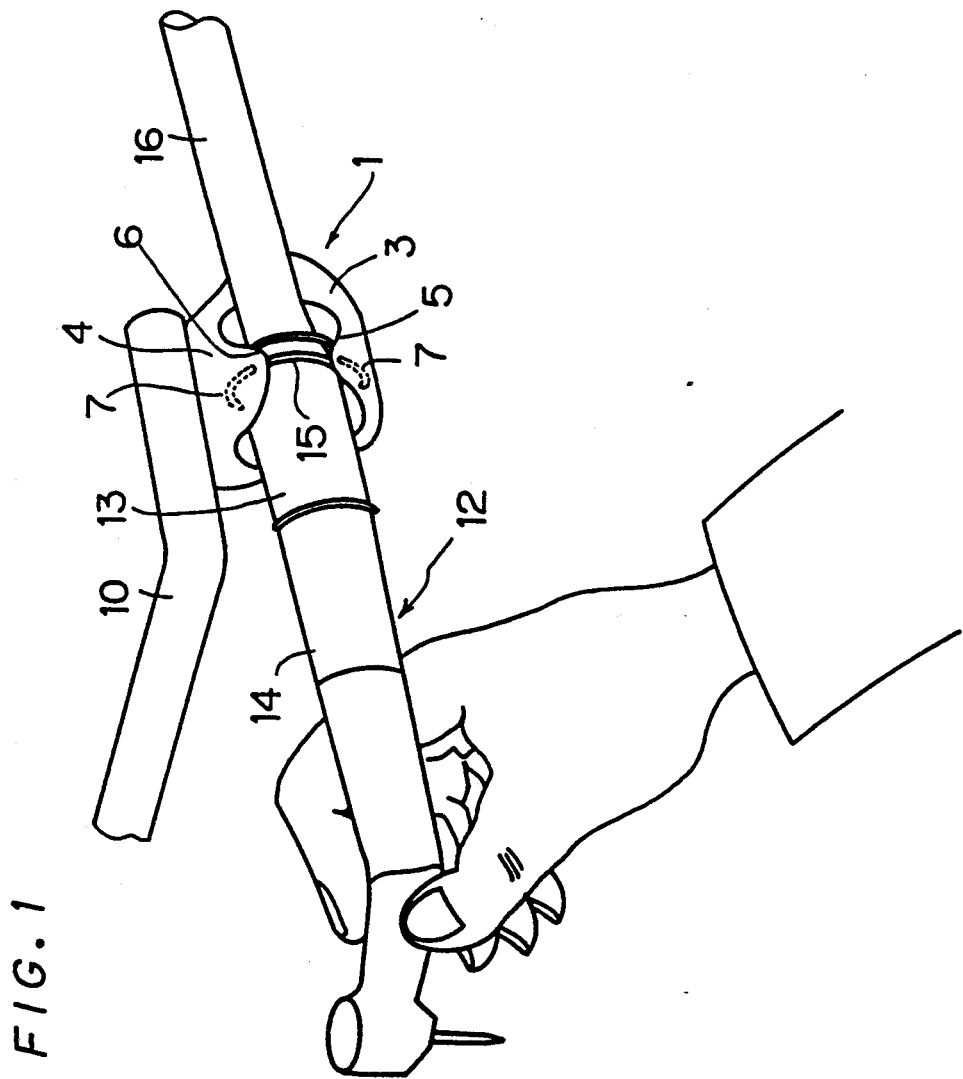
FIG. 1 is a perspective view of an example of the dental treatment assembly of the present invention.

To achieve the above-mentioned objects, the dental treatment assembly of the present invention comprises a dental handpiece and a dental handpiece holder having the following characteristics. As shown in the figures, the dental handpiece holder 1 of the present invention is characterized in that it comprises a gutter-shaped receiving seat 2, first and second grip sections 3, 4 extending from both side fringes of the receiving seat, contact sections 5, 6 formed at the leading ends of the first and second grip sections respectively and engagement grooves 7 or projections (not shown) extending across the contact sections or the peripheral areas thereof in the internal circumferential direction of the grip sections. In addition, the dental handpiece 12 of the present invention is characterized in that it comprises a ring-shaped engagement projection 15 or groove (not shown) provided on the rear outer circumference of the joint section 13 connected to a tube to engage the groove or the projection of the holder. The dental handpiece described in the present invention is not limited to those mentioned in a narrow sense, such as an air handpiece and a micro-motor handpiece. but widely includes various handpieces and syringes, such as an air scaler, an ultrasonic scaler, a vacuum syringe, a three-way syringe, an illumination handpiece and an optical polymerization handpiece.

EXAMPLES

The present invention is detailed below referring to examples and figures. In the figures, the same reference numbers designate the same corresponding sections.

FIG. 1 is a perspective view of an example of the dental treatment assembly of the present invention, illustrating that the dental handpiece attached to the handpiece holder of the present invention is held by one hand of the operator like a pencil. FIG. 2 is a plan view of the handpiece holder of the present invention shown in FIG. 1 and it also shows a supporter to or from which the holder is attached or detached. FIGS. 3 and 4 are side views of the handpiece holder shown in FIG. 2 taken in directions A and B respectively.

Referring to the figures, numeral 1 represents a handpiece holder made of resin (polycarbonate for example) or metal with superior resistance against chemicals and heat. The handpiece holder 1 has a gutter-shaped receiving seat 2 and a first grip section 3 and a second grip section 4 extending from both side fringes of the receiving seat 2. Both the first grip section 3 and the second grip section 4 are formed to be narrower toward their leading ends and have contact sections 5 and 6 at their leading ends. As also shown in the figures, the contact sections 5 and 6 face each other with a space therebetween to stably grip the handpiece 12 together with the receiving seat 2 by three-point support. The space between the contact sections 5 and 6, and the positional relationship between the contact sections 5 and 6 and the receiving seat 2 are selected to meet the above-mentioned grip relation requirements. When the handpiece 12 is pulled out nearly horizontally from the holder 1, the projection 15 disposed on the outer circumference at the rear section of the joint section 13 of the handpiece 12 engages the grooves 7 of the handpiece holder 1. The joint section 13 is retained in the holder 1 and only the handpiece 12 can be detached from the joint section 13. As a result, the handpiece can be replaced with a different one. When the handpiece 12 is pulled out obliquely upwards from the holder, however, the projection 15 disposed on the outer circumference at the rear section of the joint section 13 of the handpiece 12 does not engages the grooves 7 in the handpiece holder 1. The handpiece 12 can thus be detached from the holder 1 together with the joint section 13 and a tube 16.

The inside surfaces of the first grip section 3 and the second grip section 4, that is, the surfaces accommodating the handpiece 12 have the grooves 7 extending in the inner circumferential direction nearly perpendicular to the axial direction across the contact sections 5 and 6.

These grooves engage the projection 15 disposed on the handpiece 12. Since the handpiece 12 is also held by the receiving seat 2 and the contact sections 5 and 6, the handpiece 12 can be secured further firmly.

The engagement between the grooves 7 of the handpiece holder 1 and the projection 15 of the handpiece performs a very important function in that the engagement allows the main unit of the handpiece to be attached and detached very easily by the operator's one hand holding the handpiece like a pencil, while the multi-joint type handpiece, the main unit of which is replaced depending on the purpose of medical treatment as described above, is attached to and retained in the handpiece holder. This matter will be further detailed below.

The above-mentioned action and effect are obtained by mutually engaging the grooves 7 of the handpiece holder 1 with the projection 15 of the handpiece 12. It is therefore easily understandable that, on the contrary to the example shown in the figures, instead of the grooves 7, projections can be disposed on the holder 1, and instead of the projection 15, a ring-shaped groove can be disposed in the handpiece 12 without causing any problems, thereby obtaining the same action and effect.

Figures show a structure wherein the grooves 7 are extended in the circumferential direction of the grip section across the contact sections 5 and 6. This structure is necessary to obtain sufficient lengths for the grooves 7 in the circumferential direction of the first and second grip sections 3 and 4 which are narrowed toward their leading ends. If the lengths of the grooves 7 can be obtained adequately, the grooves can be disposed across the periphery of the contact sections 5 and 6. In addition, it is preferable that the grooves 7 are disposed in both the first and second grip sections 3 and 4. However, the groove 7 can be disposed on either grip section.

Figure 9:
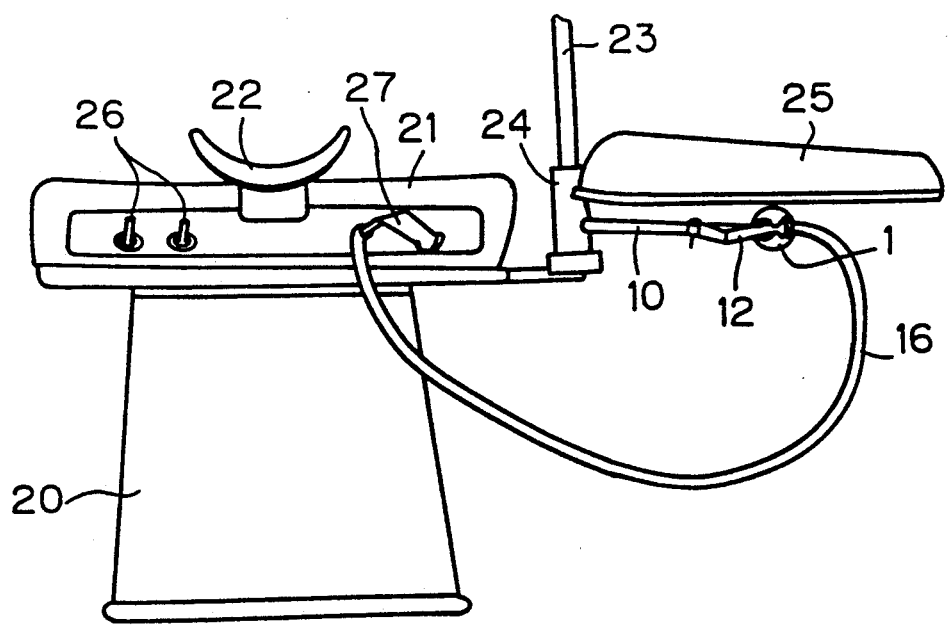
FIG. 9 is a side view of a dental chair.

In the case of the handpiece holder 1 attached to a supporter 10 which is rotatably installed on the light pole of a dental chair for example as shown in FIG. 9, the first grip section 3 positioned below has an opening 8. The main purpose of providing this opening 8 is to reduce an area where dust accumulates. On the rear side of the receiving seat 2 of the handpiece holder 1, insertion pins 9 are disposed as shown in FIG. 2 so that the handpiece holder 1 can be attached to and detached from the supporter 10. The supporter 10 has holes 11 to receive the pins 9. Instead of the insertion pins 9, insertion plates can be disposed. Furthermore, instead of disposing the pins or plates on the handpiece holder 1, pins or plates can be disposed on the supporter 10 and holes can be disposed on the handpiece holder 1 to receive the pins or plates. Attaching and detaching the handpiece holder 1 to and from the supporter 10 by using the insertion pins or plates and the holes receiving the pins or plates can be done very easily. This simple structure is advantageous in that the handpiece holder 1 is hardly contaminated and easily sterilized.

Figure 5:
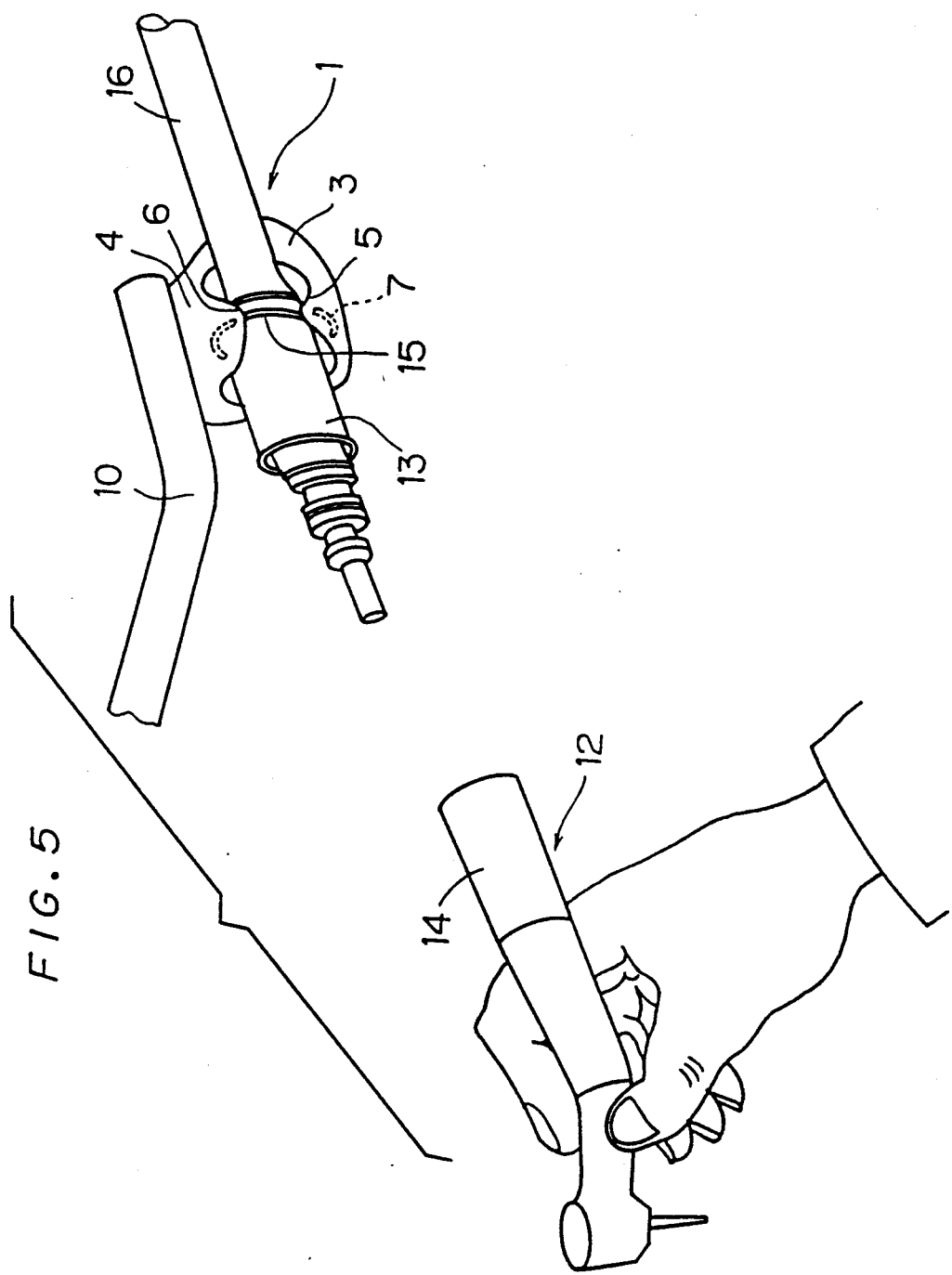
FIG. 5 is a perspective view of the handpiece of the present invention.

As described above, the ring-shaped projection 15 which engages the grooves 7 of the handpiece holder 1 is disposed at the rear section of the outer circumferential surface (corresponding to the handle mentioned in the description of the dental handpiece holder in the above-mentioned Japanese Utility Model Publication 60-33939) of the joint section 13 of the handpiece 12. The main unit 14 of the handpiece 12 is detachably connected, preferably, very easily detachably connected to the joint section 13. The quick connection joint which allows this very easy connection between the main unit of the handpiece and the joint section has been disclosed in the Japanese Utility Model Application Laid-open Publication 63-84218 and has already been well known by those skilled in the art. To the rear side of the joint section 13, that is, to the side opposite to the side connected to the main unit of the handpiece, a tube 16 containing the pipes and wires for pneumatic air, water, electricity, light, etc. are connected. FIG. 5 shows a perspective view of an example of the handpiece 12 having the above-mentioned structure, with the main unit 14 of the handpiece 12 being disconnected from the joint section 13.

When attaching the handpiece 12 to the handpiece holder 1, the handpiece 12 is inserted into the handpiece holder 1 so that the rear section of the outer circumferential surface of the joint section 13 of the handpiece 12 is held by the receiving seat 2 and the contact sections 5 and 6 of the handpiece holder 1. At the same time, the ring-shaped projection 15 on the outer circumference at the rear section of the joint section 13 of the handpiece 12 is engaged with the grooves 7 disposed in the first and second grip sections 3 and 4 of the handpiece holder 1. As a result, the handpiece 12 can be held stably by the three-point support of the receiving seat 2 and the contact sections 5 and 6 as described above, and also held securely by the engagement of the grooves 7 and the projection 15. Furthermore, the handpiece 12 can be attached easily.

Figure 6:
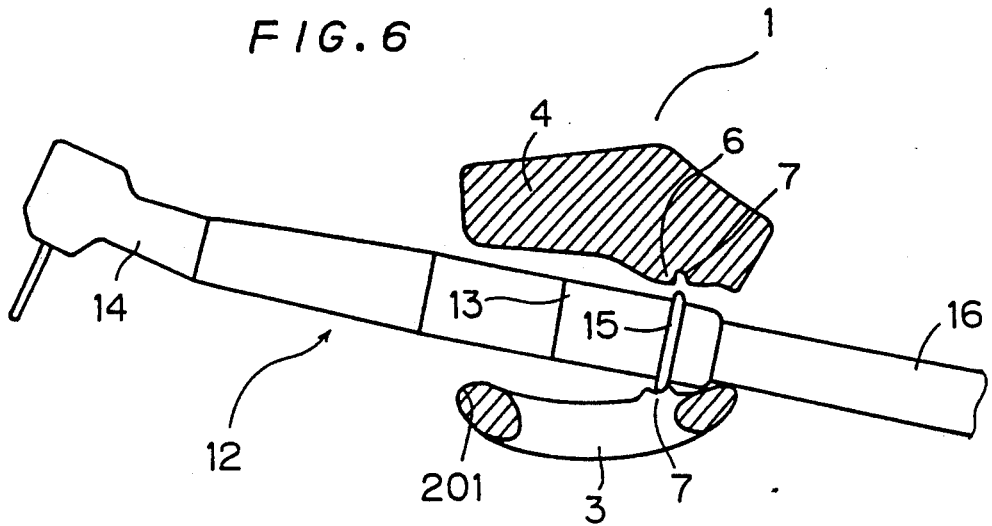
FIGS. 6 and 7 are views illustrating the extracting operation of the handpiece from the handpiece holder of the present invention.

When taking out the handpiece 12 from the handpiece holder 1, the handpiece 12 being held like a pencil should be inclined and pulled upwards obliquely as shown in FIG. 6 (the cross section of the handpiece holder 1 is taken on line X-O-Y of FIG. 3). The grooves 7 are disengaged from the projection 15 of the handpiece 12 and the handpiece 12 can be taken out easily.

Figure 7:
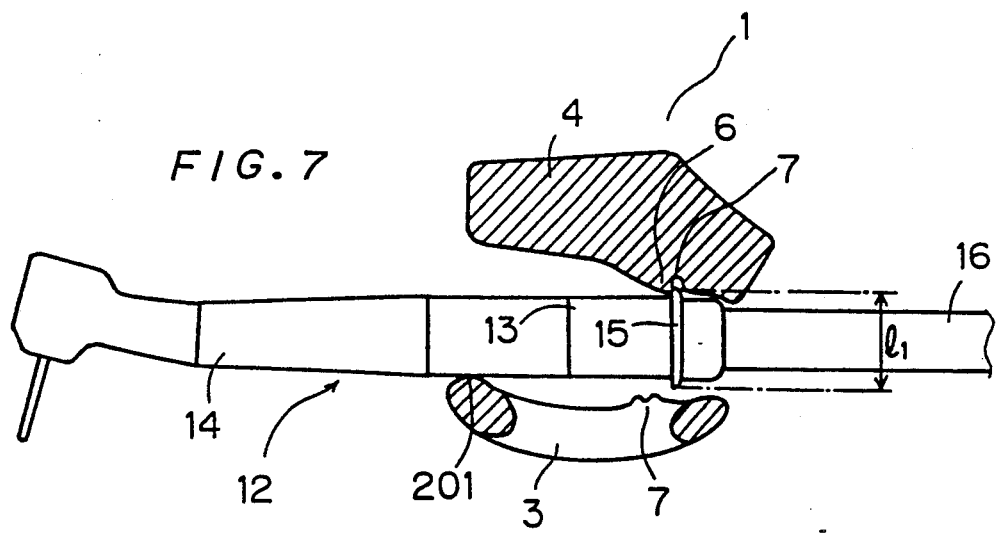

Instead of pulling out the handpiece 12 upwards obliquely, when the handpiece 12 is pulled out nearly horizontally in the axial direction of the receiving seat 2 as shown in FIG. 7 (the cross section of the handpiece holder 1 is taken on line X-O-Y of FIG. 3), the grooves 7 are engaged with the projection 15 of the handpiece 12 and the handpiece 12 is retained by the handpiece holder 1 and cannot be taken out.

These retaining and pulling-out operations between the handpiece holder 1 and the handpiece 12 are further detailed below. In the retaining condition shown in FIG. 7, the movement of the handpiece 12 in the axial direction is prevented since the projection 15 engages the grooves 7 of the handpiece holder 1. The movement in the vertical direction also prevented, that is, the handpiece 12 is attached nearly horizontally to the handpiece holder 1, since the forward rotation moment around the front end 201 of the receiving seat 2 is restricted by the contact sections 5 and 6 due to the fact that the center of gravity of the handpiece 12 is located ahead of the front end 201 of the receiving seat 2. When the front section of the handpiece 12 is held and inclined upwards by the operator as shown in FIGS. 5 and 6, the projection 15 of the joint section 13 of the handpiece 12 is disengaged from the grooves 7 of the handpiece holder 1. The distance between the contact sections 5 and 6 is determined to be larger than the outer diameter $l_2$ of the tube 16 connected to the handpiece 12 and smaller than the outer diameter $l_1$ of the projection 15 of the joint section 13 of the handpiece 12.

With this structure, when the handpiece 12 can be detachably connected to the main unit 14 of the handpiece 12, in particular when the main unit 14 of the handpiece 12 can be connected to the joint section 13 via a quick connection joint which allows very easy connection, the main unit 14 of the handpiece 12 can be taken out from the joint section 13 and replaced with another main unit while the outer circumferential surface of the joint section 13 of the handpiece 12 is held stably and retained by the handpiece holder 1 after the handpiece 12 is pulled out horizontally as described above. Moreover, since the joint section 13 is held stably and retained by the holder 1, the main unit 14 of the handpiece 12 can be attached and detached by the operator's one hand which holds the main unit like a pencil.

It is noted that the above-mentioned attaching and detaching of the main unit of the handpiece are made possible by the feature that the handpiece holder 1 of the present invention is short in the axis direction and holds the handpiece 12 in a short range, more particularly, by the feature that the holder 1 holds only the outer circumferential surface of the joint section 13 of the handpiece 12. This feature will be understood easily when the handpiece of the present invention is compared with the above-mentioned conventional dental handpiece holder which is long in the axial direction and holds its handpiece in the range from the grip section (belonging to the main unit of the handpiece) to the handle section (belonging to the joint section) of the handpiece at the receiving sections of the leading and trailing ends of the holder.

Figure 8:
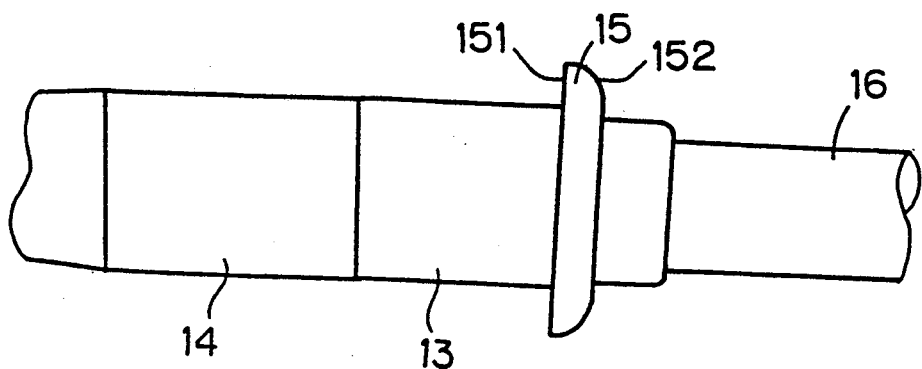
FIG. 8 is a side view illustrating the shape of the engagement projection provided on the joint section of the handpiece of the present invention.

The vertical cross-section of the projection disposed on the outer circumference at the rear section of the joint section of the handpiece is desired to have a shape shown in FIG. 8 and detailed below to facilitate the engagement and disengagement between the projection 15 of the handpiece 12 and the grooves 7 of the handpiece holder 1 at the time when the handpiece 12 is pulled obliquely upwards or horizontally as described above. More specifically, a steep wall surface 151 is provided on the front side of the projection 15, at least in the proximity of the top of the projection 15, so that the projection 15 can engage the grooves 7 securely and stably when the handpiece 12 is pulled out nearly horizontally. On the rear side (close to the tube 16) of the projection 15, a gradually inclined surface 152 which is gradually curved from the top of the projection 15 is provided so that the projection 15 can be easily disengaged from the grooves 7 and the handpiece 12 can be pulled out upwards when the handpiece 12 is inclined. In the example shown in the figures, the engagement grooves 7 are disposed in the handpiece holder 1 and the ring-shaped engagement projection 15 is disposed on the outer circumference of the joint section 13 of the handpiece 12. However, the present invention is not limited to this structure. The engagement projection 15 can be disposed on the handpiece holder 1 and the ring-shaped engagement groove 7 can be disposed on the outer circumference of the joint section 13 of the handpiece 12.

FIG. 9 is a side view of a dental chair 20 viewed from the head rest 22 thereof. In this figure, the handpiece 12 is held by the handpiece holder 1 of the present invention attached to the supporter 10 which is rotatable via a sleeve 24 fitted over a light pole 23 standing on the side of the main unit 21 of the dental chair 20. Numeral 25 represents a tray and numerals 26 and 27 represent syringes and a vacuum syringe respectively.

Figure 10:
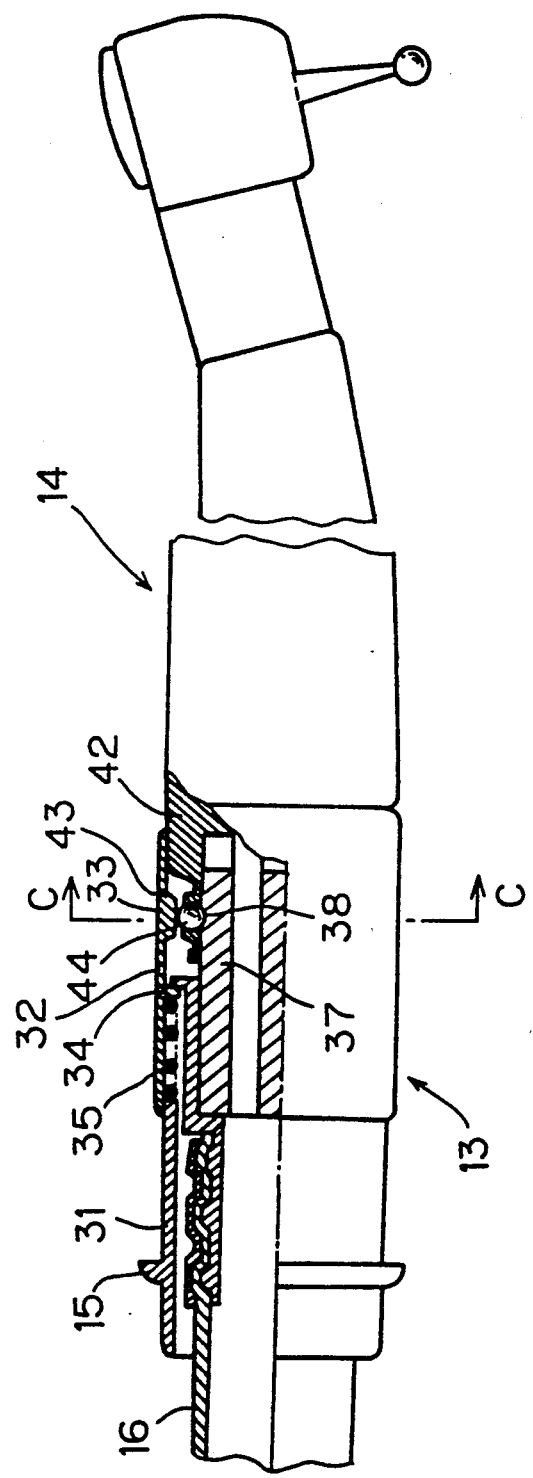
FIG. 10 is a partial cross-sectional sectional side view of the handpiece wherein the main unit of the handpiece is connected to its joint section by using a quick connection joint.
Figure 11:
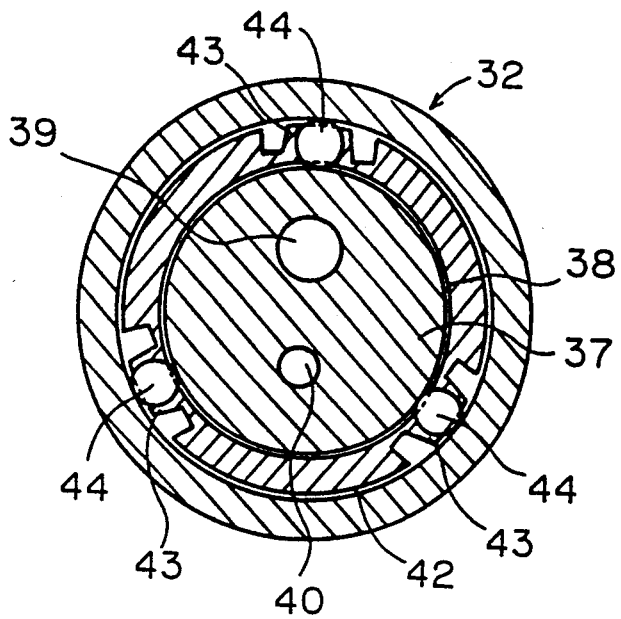
FIG. 11 is a cross-sectional view taken on line C—C of FIG. 10.
Figure 12:
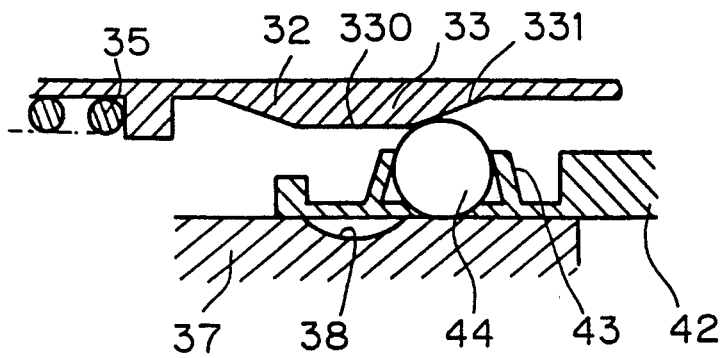
FIG. 12 is a cross-sectional view illustrating the engagement mechanism of the quick connection joint and FIG. 13 is another cross-sectional view illustrating the engagement mechanism of the quick connection joint.
Figure 13:
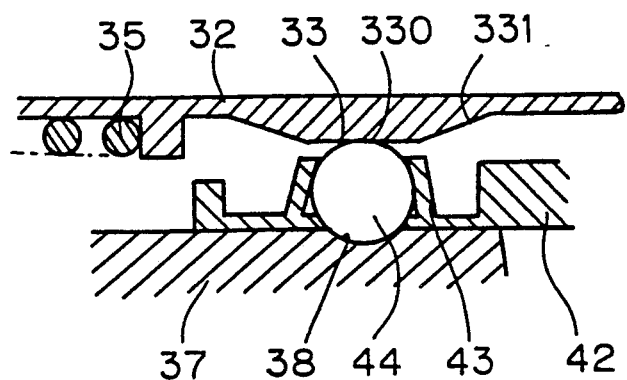

FIGS. 10 to 13 show an example which uses a quick connection joint to connect the main unit 14 of the handpiece 12 and the joint section 13. FIG. 10 is a partially sectional side view of the handpiece 12 wherein the quick connection joint is used to connect the main unit 14 of the handpiece 12 and the joint section 13. FIG. 11 is a sectional view of the handpiece 12 taken on line C—C of FIG. 10. FIGS. 12 and 13 are sectional views illustrating the engagement mechanism of the quick connection joint.

In these figures, numeral 31 represents the outer cylinder of the joint section 13. The above-mentioned projection 15 is disposed on the rear side of the outer circumferential surface of the outer cylinder 31. Numeral 32 represents a slide ring which can slide over the outer cylinder 31. On the inner circumferential surface on the front side of the slide ring 32, a trapezoidal projection 33 is disposed. A spring 35 is inserted between the front end of the outer cylinder 31 and the spring holder 34 of the slide ring 32 to push the slide ring 32 toward the front end side. Numeral 36 represents a sleeve and its rear end side is connected to the tube 16 and its front end side is connected to a male member 37 via screw. On the outer circumferential surface of the male member 37, an engagement groove 38 is disposed. Numeral 39 represents a pneumatic air passage for driving a turbine. Numeral 40 represents a water supply passage.

At the rear end section of the female member 42 of the main unit 14 of the handpiece 12, three ball holders 43 are formed at 120 degrees intervals to hold engagement balls 44.

To attach the main unit 14 of the handpiece 12 to the joint section 13, the rear end section of the female member 42 is inserted into the space between the male member 37 and the slide ring 32. At this time, as shown in FIG. 12, the engagement balls 44 contact the inclined surface 331 of the trapezoidal projection 33 on the inner surface of the slide ring 32. When the female member 42 is pushed further continuously against the force of the spring 35, the slide ring 32 is pushed backward and the engagement balls 44 are inserted into the engagement groove 38 of the male member 37.

When the engagement balls 44 are inserted into the engagement groove 38 as shown in FIG. 13, the slide ring 32 is returned forward by the force of the spring 35, and the top section 330 of the trapezoidal projection 33 pushes and holds the engagement balls 44 in the engagement groove 38. As a result, the main unit 14 of the handpiece 12 cannot be separated from the joint section 13 if the force for separation is below the force of the spring 35. Furthermore, since the engagement balls 44 can rotate along the engagement groove 38, the main unit 14 of the handpiece 12 is relatively rotatable with the joint section 13.

When detaching the main unit 14 of the handpiece 12 from the joint section 13, the main unit 14 of the handpiece 12 is held horizontally and pulled forward against the force of the spring 35 while the projection 15 of the joint section 13 of the handpiece 12 remains engaged with the grooves 7 of the handpiece holder 1. By this operation, the condition shown in FIG. 13 is changed to the condition shown in FIG. 12 and the engagement balls 44 are moved from the insertion position. As a result, only the main unit 14 of the handpiece 12 can be separated from the joint section 13 while the handpiece holder 1 remains engaged with the joint section 13.

Since the handpiece holder of the present invention holds the handpiece by the three-point support using the receiving seat and the contact sections 5 and 6 and by the engagement with the handpiece via the grooves or projection as described above, the holding performance is secure and stable. In addition, the length of the handpiece holder in the axial direction is made significantly shorter than that of the conventional holder. As a result, the length of the handpiece section directly gripped by the holder is thus shortened when the handpiece is attached to the holder. The holder is thus required only to hold the section near the ring-shaped projection or groove disposed on the outer circumference at the rear section of the joint section of the handpiece.

In this way, when the handpiece is attached to the handpiece holder, the possibility of contacting the operator's hand holding the grip section of the main unit of the handpiece like a pencil to the handpiece holder is significantly made smaller. Consequently, the possibility of contaminating the holder by the operator's hand, or on the contrary the possibility of contaminating the operator's hand by the holder can be reduced significantly. Moreover, the handpiece holder of the present invention is short in the axial direction and simple in structure and easily sterilized. In combination with these advantages, the present invention is greatly beneficial to the improvement of the sanitation control in dental treatment.

With the present invention, when the handpiece attached to the handpiece holder is inclined and pulled out obliquely upwards, the handpiece can be taken out easily and when an attempt is made to pull out the handpiece in the horizontal direction, the engagement projection and groove disposed on the handpiece and the handpiece holder make firm engagement to retain the handpiece in the handpiece holder as described above.

With this structure, when replacing the handpiece comprising the main unit of the handpiece connected to the joint section via the quick connection joint, the operator holds the handpiece attached to the handpiece holder with one hand like a pencil and pulls the handpiece in the horizontal direction. While the joint section of the handpiece is retained in the handpiece holder, the operator pulls the main unit of the handpiece further strongly with his one hand holding the main unit like a pencil to release the quick connection joint and to separate the main unit of the handpiece from the joint section. By this operation, the operator can detach the main unit of the handpiece from the joint section with his one hand and can replace the main unit with that of another handpiece. In other words, the handpiece holder of the present invention can also be used as the holding member of the joint section that is used for the replacement of the main unit of the handpiece.

As described above, with the present invention, the handpiece holder can be used as the holding member of the joint section that is used for the replacement of the main unit of the handpiece. Moreover, the main unit of the handpiece can be replaced by the operator without making his hand contact with the joint section of the handpiece or the tube and other parts connected to the handpiece. Consequently, the present invention is greatly beneficial to prevent contamination and enhance sanitation.

We claim:

1. A dental treatment assembly comprising a dental handpiece comprising a ring-shaped engagement projection or groove which is disposed on the outer circumference at a rear section of a joint section connected to a tube, and a dental handpiece holder comprising a gutter-shaped receiving seat, first and second grip sections extending from both side fringes of said receiving seat, contact sections formed at the leading ends of said first and second grip sections respectively and an engagement groove or projection extending across said contact sections or the peripheral areas thereof in the internal circumferential direction of said grip sections for engagement with said ring-shaped engagement projection or groove which is disposed on the outer circumference of said joint section connected to the said tube.

2. A dental treatment assembly according to claim 1 wherein said tube is detachably connected at a front section to a main unit of the handpiece to be gripped like a pencil.

3. A dental treatment assembly according to claim 2 wherein said first and second grip sections are provided between front and rear sections in an axial direction of said receiving seat.

* * * * *